(12) United States Patent
Chowers et al.

(10) Patent No.: US 6,815,414 B2
(45) Date of Patent: Nov. 9, 2004

(54) **PHARMACEUTICAL COMPOSITIONS FOR THE TREATMENT OF *HELICOBACTER PYLORI*-ASSOCIATED DISORDERS**

(75) Inventors: Michal Y. Chowers, Tzufit (IL); Yehuda Chowers, Tzufit (IL)

(73) Assignee: Vecta Ltd., Rehovot (IL)

( * ) Notice: Subject to any disclaimer, the term of this patent is extended or adjusted under 35 U.S.C. 154(b) by 0 days.

(21) Appl. No.: 09/738,948

(22) Filed: Dec. 15, 2000

(65) Prior Publication Data

US 2003/0069188 A1 Apr. 10, 2003

Related U.S. Application Data

(63) Continuation of application No. PCT/IL99/00335, filed on Jun. 17, 1999.
(60) Provisional application No. 60/147,195, filed on May 20, 1999, and provisional application No. 60/089,770, filed on Jun. 18, 1998.

(51) Int. Cl.[7] .................. A61K 38/00; A61K 49/00; A01N 37/18
(52) U.S. Cl. .................. 514/2; 514/12; 514/17; 514/18; 530/300; 424/9.1; 435/7.1; 435/243
(58) Field of Search .................. 514/2, 12, 17, 514/18, 13, 16; 435/7.1, 243, 7.23, 7.32, 252.1; 424/9.1; 530/300, 330, 328, 326, 324

(56) References Cited

U.S. PATENT DOCUMENTS 4,794,103 A * 12/1988 Bertolini .................. 514/12

OTHER PUBLICATIONS

Beales, I. and Calam, J. "*Helicobacter pylori* infection and tumour necrosis factor–α increase gastrin release from human gastric antral fragments," *European Journal of Gastroenterology & Hepatology* 9:773–777 (1997).

Chowers, M. et al., "Human Gastrin: A *Helicobacter pylori*–Specific Growth Factor," *Gastroenterology* 117:1113–1118 (1999).

El–Omar, E. et al., "Eradicating *Helicobacter pylori* infection lowers gastrin mediated acid secretion by two thirds in patients with duodenal ulcer," *Gut* 34:1060–1065 (1993).

Harris, A.W. et al., "Eradication of *Helicobacter pylori* in patients with duodenal ulcer lowers basal and peak acid outputs to gastrin releasing peptide and pentagastrin," *Gut* 38:663–667 (1996).

Konturek, J.W. et al., "Eradication of *Helicobacter pylori* restores the inhibitory effect of choloecystokinin on postpradial gastrin release in duodenal ulcer patients," *Gut* 37:482–487 (1995).

Yamashita, K. et al., "Inhibitory Effect of Somatostatin on *Helicobacter pylori* Proliferation In Vitro," *Gastroenterology* 115:1123–1130 (1998).

Database WPI; Section Ch, Week 199738; Derwent Publications, Ltd., London, GB; Class B03, AN 1997–410809; XP002126333 & JP 09 183764 A (Morishita Roussel KK), Jul. 15, 1997; abstract.

* cited by examiner

Primary Examiner—Christopher F. Low
Assistant Examiner—Chih-Min Kam
(74) Attorney, Agent, or Firm—Winston & Strawn LLP (57) ABSTRACT

The invention relates to pharmaceutical compositions and methods for treating and/or preventing *Helicobacter pylori*-associated disorders, particularly disorders of the gastrointestinal tract. The pharmaceutical compositions comprise as active ingredient a therapeutically effective amount of a compound which inhibits the growth-enhancing effect of gastrin on *H. pylori*. The active ingredient may specifically be a compound which is capable of inhibiting gastrin uptake by *H. pylori*, and/or which is an antagonist of the human or *H. pylori* gastrin receptor.

16 Claims, 5 Drawing Sheets

```
                            SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Trp Met Asp Phe
```

PHARMACEUTICAL COMPOSITIONS FOR THE TREATMENT OF *HELICOBACTER PYLORI*-ASSOCIATED DISORDERS

RELATED APPLICATIONS

This application is a continuation of International Application No. PCT/IL99/00335, which designated the United States and was filed on Jun. 17, 1999, published in English, which claims the benefit of U.S. Provisional Application No. 60/147,195 filed on May 20, 1999 and U.S. Provisional Application No. 60/089,770 filed on Jun. 18, 1998. The entire teachings of the above applications are incorporated herein by reference.

FIELD OF THE INVENTION

The invention relates to pharmaceutical compositions for the treatment and/or prevention of *Helicobacter pylori*-associated disorders and to methods of treating such disorders in patients in need thereof.

BACKGROUND OF THE INVENTION

*Helicobacter pylori* (*H. pylori*) infection is associated with several benign and malignant human diseases [Dooley CP, et al., N Engl J Med (1989) 321:1562–1566; Carrick J, et al., Gut (1989) 30:790–797; Nomura A, et al., N Engl J Med (1991) 325:1132–1136 [see comments]; Nomura A, et al., Ann Intern Med (1994) 120:977–981 [see comments]; Zucca E, et al., N Engl J Med (1998) 338:804–810]. However, symptomatic infection is only the tip of the iceberg, the majority of infected individuals remain asymptomatic. Moreover, if untreated, infection may last for decades [Peterson W L and Harford W V, (1991) 86:671–675], representing a successful host-parasite relationship. This favorable interaction is reflected in a high prevalence of infection ranging between 50% in developed to 90% in developing countries [Graham D Y, et al. Dig Dis Sci (1991) 36:1084–1088; Taylor D N and Blaser M J, Epidemiol Rev (1991) 13:42–59].

*H. pylori* resides within the mucous layer of the human gastric mucosa. Due to extremely low pH, the stomach is a hostile environment to most other microorganisms. The ability of *H. pylori* to flourish in the stomach has been attributed to protective mechanisms such as its production of urease, protecting the bacterium from gastric acidity by creating a basic microenvironment [Taylor D N and Blaser M J, Epidemiol Rev (1991) 13:42–59]. However, it has now been reasoned, that *H. pylori* might have evolved a way to gain growth advantage in this particular niche of the stomach, possibly by exploiting a gastric factor. A logical candidate would be one that is upregulated by *H. pylori* infection.

One such factor is the gastric hormone gastrin. Gastrin is produced as a prohormone by G cells located within the gastric antrum. The prohormone is later processed to shorter peptides, the most abundant of which is 17 amino acids long, termed gastrin 17 (G17) [Eaton K A, et al, Infect Immun (1991) 59:2470–2475]. The major role attributed to gastrin within the gastric tissue is the regulation of acid secretion. Following infection, gastrin levels are found to be consistently elevated and normal physiologic negative feedback control of secretion is lost. Further, following *H. pylori* eradication, gastrin levels are reduced and normal feedback control of gastrin secretion is restored [Graham D Y, et al., Am J Gastroenterol (1990) 85:394–398; El-Omar E, et al., Gut (1993) 34:1060–1065 [see comments]; Konturek J W, et al, Gut (1995) 37:482–487].

Interest in the changes of gastrin secretion and control have been directed to its role in acid production, and the resulting peptic pathology. However, the present work was focused on the possible interactions between gastrin and *H. pylori*.

As will be shown hereafter, gastrin positively stimulates the growth of *H. pylori*, a finding which further exemplifies the successful adaptation of *H. pylori* to the human host, and provides the basis for the present invention.

SUMMARY OF THE INVENTION

The present invention relates to pharmaceutical compositions for the treatment and/or prevention of *H. pylori*-associated disorders comprising as active ingredient a therapeutically effective amount of a compound which inhibits the growth-enhancing effect of gastrin on *H. pylori*, particularly *H. pylori*-associated gastrointestinal disorders, such as *H. pylori*-associated gastric and/or duodenal peptic diseases. The pharmaceutical compositions of the invention may optionally further comprise pharmaceutically acceptable carriers, adjuvants or diluents.

The active ingredient in the pharmaceutical compositions of the invention may be a compound which is capable of inhibiting gastrin uptake by *H. pylori*, particularly compounds which are competitive inhibitors of gastrin uptake by *H. pylori*, or antagonists of the human or *H. pylori* gastrin receptor. In preferred embodiments, the active compound in the pharmaceutical compositions of the invention is a peptide. Preferred peptides are synthetic analogues of gastrin or of a fragment of gastrin, preferably of G17, and most preferred are peptides comprising the amino acid sequence: Trp-Met-Asp-PheNH$_2$ (SEQ ID NO:1), such as pentagastrin or cholecystokinin (CCK)-8.

In other embodiments the pharmaceutical compositions of the invention may comprise as the active ingredient a non-peptidic antagonist of the human or *H. pylori* gastrin receptor.

In yet a further aspect, the invention relates to a method for the treatment and/or prevention of *H. pylori*-associated disorders in a patient in need of such treatment, comprising administering to said patient a therapeutically effective amount of a compound which inhibits the growth-enhancing effect of gastrin on *H. pylori* or a therapeutically effective amount of a composition according to the invention.

The method of the invention may be used for the treatment and/or prevention of *H. pylori*-associated gastrointestinal disorders.

Yet further, the invention relates to use of a compound which inhibits the growth-enhancing effect of gastrin on *H. pylori* in the preparation of a pharmaceutical composition for the treatment of *H. pylori*-associated disorders. In the use according to the invention, the said compound may be a synthetic analogue of G17, preferably comprising the amino acid sequence: Trp-Met-Asp-PheNH$_2$ (SEQ ID NO:1). Alternatively, the compound may be a non-peptidic antagonist of the human or *H. pylori* gastrin receptor.

BRIEF DESCRIPTION OF THE FIGURES

FIGS. 1A to 1B *H. pylori* growth kinetics in the presence of gastrin.
Bacteria were grown in liquid media, using microaerophilic conditions with increasing gastrin concentrations. Growth rate was assessed by optical density (OD). T indicates time in hours.

FIGS. 2A to 2F Gastrin growth stimulation is bacterial and peptide specific.

Growth kinetic analysis of different bacteria with gastrin:

Bacteria were grown using liquid media and growth rate assessed by optical density (OD). T indicates time in hours. Except the aerobic conditions used for the growth of E. coli, all growth conditions were identical. One experiment representative of three (each performed with a different isolate).

H. pylori (H.P.), E. coli (E.C.), S. pneumonia (S.P.) and C. jejuni (C.J.) bacteria were incubated for 45 minutes with $^{125}$I-labeled gastrin. Incubation was at 4° C. or 37° C. Following initial incubation, proteinase K (P.K) was added for 30 minutes, after which bacteria were washed and blotted. One experiment representative of two.

Bacteria were incubated in the presence of 500 nmo/l $^{125}$I-labeled gastrin and increasing concentrations of either unlabeled gastrin (G), CCK-8 (CCK), pentagastrin (Pen), somatostatin (Som) or EGF for 45 min. Bacteria were washed and radioactivity remaining in bacterial pellets was determined. One experiment representative of three.

DETAILED DESCRIPTION OF THE INVENTION

H. pylori infection is associated with duodenal ulcer, gastric ulcer, gastric adenocarcinoma and B cell lymphoma. It has also been implicated in cardiovascular diseases, particularly atherosclerosis and ischemia, since it has been shown that the infection is more abundant in patients suffering from these diseases. The bacterium resides within the gastric mucosa, a unique niche hostile to other microorganisms. Gastrin, a gastric hormone, is consistently elevated following H. pylori infection. It has now been found that human gastrin stimulates H. pylori growth in a specific, dose-dependent mechanism, which suggests a novel approach to treating H. pylori infections.

As demonstrated in the following Examples, the human hormone gastrin significantly stimulated H. pylori growth in a dose-dependent manner. This effect was reproducible in all bacterial isolates studied. Growth stimulation occurred at physiological gastrin concentrations found in the blood and gastric lumen [Mueller C R, et al., Surgery (1991) 110:1116–1124; Yamashita K, et al., Gastroenterology (1998) 115:1123–1130].

The uptake of gastrin by H. pylori and the stimulatory growth effect were highly specific and were not detected with control bacteria or by other peptides present in the gastric antrum or lumen. Moreover, cold ligand inhibition suggested the effect was mediated via a specific gastrin binding site. Gastrin, CCK-8 and pentagastrin have structural similarity and activate human gastrin/CCKB receptors. In the present experiments, both CCK-8 and pentagastrin competed with gastrin on the binding to H. pylori, but did not stimulate bacterial growth. The competition by structurally related compounds supports the suggestion that a specific binding site is involved in gastrin uptake by H. pylori. The fact that biological activity could be obtained only with gastrin, reiterates the specific interaction of H. pylori with this hormone.

In light of the present findings, host parasite interaction between the human host and H. pylori could be viewed as having evolved to exploit gastrin by the bacterium. H. pylori preferentially colonizes the gastric antrum, the anatomic location of gastrin producing G cells [Bayerdorffer E, et al., Gastroenterology (1992) 102:1575–1582]. In addition, infection results in hypergastrinemia and a loss of negative feedback control on gastrin secretion, potentially leading to the continuous exposure of bacteria to high levels of gastrin.

The histologic hallmark of H. pylori infection is chronic antral inflammation. As a result of this inflammation, increased levels of pro-inflammatory cytokines have been documented [Crabtree J E, et al., Gut (1991) 32:1473–1477; Karttunen R, et al., Gut (1995) 36:341–345; Noach L A, et al., Scand J Gastroenterol (1994) 29:425–429; Crabtree J E, et al., Scand J Immunol (1993) 37:65–70]. Using in vitro cultures, it was shown that endocrine cells can produce gastrin in response to stimulation with such inflammatory cytokines [Lehmann F S, et al., Am J Physiol (1996) 270:783–788; Weigert N, et al., Gastroenterology (1996) 110:147–154; Beales I L, et al., Eur J Gastroenterol Hepatol (1997) 9:773–777; Wallace J L, et al Am J Physiol (1991) 261:G559–564]. Thus, H. pylori may actually benefit from the host immune response, which initiates up-regulation of a bacterial growth factor.

Models based on H. pylori characteristics and host parasite interaction have been proposed. Lee suggested that the exceptionally small size of the H. pylori genome and the small number of regulatory genes might indicate that the bacterium is well adapted to a highly specific single habitat [Lee A, N Engl J Med (1998) 338:832–833]. The finding that H. pylori utilizes gastrin, a gastric hormone, concurs with this proposal. Furthermore, the chronicity and persistence of H. pylori infection in the human host led Blaser to suggest that the interaction between bacterium and host is mutually regulated. Such regulation implies co-evolution [Blaser M J, J Clin Invest (1997) 100:759–762]. Increased gastrin secretion as a consequence of infection and the possible exploitation of gastrin by the bacterium fit this concept.

Therapy of peptic ulcer disease prior to the discovery of the central role of H. pylori, was based on agents capable of reducing gastric acidity. Based on meta analysis of multiple trails aimed at healing peptic ulcers, it was shown that there is no advantage in elevating the pH to above 3, for more than 18 hours daily. Still, several groups of agents are used for reducing the stomach acidity. Most important of these agents are the H2 receptor antagonists and proton pump inhibitors. H2 receptor antagonists act by blocking histamine H2 receptors on the parietal cells. Proton pump inhibitors act by inhibition of the parietal cell $H^+K^+$ ATPase, responsible for acid secretion from the cells.

Current therapies of H. pylori infections usually consist of combinations of two antibiotic agents together with an adjunctive agent, which is usually either a proton pump inhibitor or bismuth. Antibiotic resistance of H. pylori is widespread, with increasing prevalence [Hazell, S L, Eur J Clin Infect Dis (1999) 18:83–86]. H. pylori-associated infection is a rather common phenomenon, resulting in a massive use of antibiotics, sometimes prescribed also to a symptomatic carriers. This massive use may exhaust the option of treatment of this disease by currently available drugs, and the resistance of the bacterium may later adversely affect the extent of success of therapy of *H. pylori* infection, as well as other infectious agents that may become resistant, as a secondary effect of extensive use of antibiotics.

The present findings suggest that gastrin may be the factor on which *H. pylori* thrives, and in its absence, the bacterium will not be able to survive in the gastric antrum. The growth benefit provided to *H. pylori* by gastrin, may be the reason for the ability of this bacterium to flourish in this hostile habitat.

It is this newly discovered relationship between gastrin and *H. pylori*, which provides the basis for alternative, non-antibiotic-based improved therapies of various diseases associated with *H. pylori* infection, particularly those of the gastrointestinal tract.

Thus, the invention relates to a pharmaceutical composition for the treatment and/or prevention of *H. pylori*-associated disorders comprising as active ingredient a therapeutically effective amount of a compound which inhibits the growth-enhancing effect of gastrin on *H. pylori*, optionally further comprising pharmaceutically acceptable carriers, adjuvants or diluents.

The pharmaceutical composition of the invention may be particularly suitable for the treatment and/or prevention of *H. pylori*-associated gastrointestinal disorders, specifically, *H. pylori*-associated gastric and/or duodenal peptic diseases. In addition the compositions of the invention may be used for the treatment of gastritis, duodenitis, non-ulcer dyspepsia, mucosal-associated lymphoid tissue lymphoma, for the prevention of gastric carcinoma and in the treatment of atherosclerotic cardiovascular diseases.

The active ingredient in the pharmaceutical compositions of the invention is preferably a compound which is capable of inhibiting gastrin uptake by *H. pylori*. Such compound may be a competitive inhibitor of gastrin uptake by *H. pylori*, or an antagonist of the human or *H. pylori* gastrin receptor.

In preferred embodiments, the active compound comprised in the pharmaceutical composition of the invention is a peptide. Preferred peptides may be a synthetic analogue of gastrin or of a fragment of gastrin, preferably comprising an amino acid sequence corresponding to the C-terminal of gastrin or to a gastrin fragment, preferably G17. Such preferred peptides comprise the amino acid sequence: Trp-Met-Asp-PheNH$_2$ (SEQ ID NO:1). Particular examples of synthetic peptides which may be used as the active principal in the compositions of the invention are pentagastrin or cholecystokinin (CCK)-8.

Pentagastrin is a synthetic gastrin analogue that exhibits the biological activity of gastri. The main clinical use of this compound was for stimulation of acid secretion in a diagnostic test required for exclusion of achlorhydria (acid stimulation occurs within 10 minutes and peaks within 20–30 minutes). Pentagastrin replaced the use of histamine in such tests, because it has milder side effects.

Synthetic peptides used in the compositions of the invention may be in the form of a dimer, a multimer or in a constrained conformation, in which the constrained conformation is obtained by internal bridges, short-range cyclizations, extension or other chemical modification.

In a further embodiment, the active compound comprised in the pharmaceutical compositions of the invention may be a non-peptidic antagonist of the human or *H. pylori* gastrin receptor.

In a further aspect, the present invention relates to a method for the treatment and/or prevention of *H. pylori*-associated disorders in a patient in need of such treatment, comprising administering to said patient a therapeutically effective amount of a compound which inhibits the growth-enhancing effect of gastrin on *H. pylori* or a therapeutically effective amount of a composition according to the invention.

The method of the invention is particularly suitable for the treatment and/or prevention of *H. pylori*-associated gastrointestinal disorders, but is not limited thereto.

The compound to be administered by the method of the invention is a compound which capable of inhibiting gastrin uptake by *H. pylori*. Particular compounds may be competitive inhibitors of gastrin uptake by *H. pylori* and/or antagonists of the human or *H. pylori* gastrin receptor.

In preferred embodiments, the compound to be administered is a peptide, preferably a synthetic analogue of gastrin or of a fragment of gastrin, preferably of G17. More preferred peptides of the amino acid sequence: Trp-Met-Asp-PheNH$_2$ (SEQ ID NO:1), are for example pentagastrin or cholecystokinin (CCK)-8. In other embodiments of the method of the invention the compound to be administered may be a non-peptidic antagonist of the human or *H. pylori* gastrin receptor.

Still further, the invention relates to use of a compound which inhibits the growth-enhancing effect of gastrin on *H. pylori* in the preparation of pharmaceutical compositions for the treatment of *H. pylori*-associated disorders, particularly in the preparation of pharmaceutical compositions for the treatment of *H. pylori*-associated gastrointestinal disorders.

All of the compounds referred to above may be used in the preparation of pharmaceutical compositions according to the use of the invention.

The pharmaceutical compositions of the invention will generally contain salts, preferably in physiological concentration, such as PBS (phosphate-buffered sale), or sodium chloride (0.9% w/v), and a buffering agent, such as phosphate buffer in the above PBS. The preparation of pharmaceutical compositions is well known in the art, see e.g., U.S. Pat. Nos. 5,736,519, 5,733,877, 5,554,378, 5,439,688, 5,418,219, 5,354,900, 5,298,246, 5,164,372, 4,900,549, 4,755,383, 4,639,435, 4,457,917 and 4,064,236. The active ingredient of the pharmaceutical compositions of the present invention, for example a peptide, or pharmacologically acceptable salts thereof, is preferably mixed with an excipient, carrier, diluent, and optionally, a preservative or the like pharmacologically acceptable vehicles as known in the art, see e.g., the above U.S. patents. Examples of excipients include, glucose, mannitol, inositol, sucrose, lactose, fructose, starch, corn starch, microcrystalline cellulose, hydroxypropylcellulose, hydroxypropyl-methylcellulose, polyvinylpyrrolidone and the like. Optionally, a thickener may be added, such as a natural gum, a cellulose derivative, an acrylic or vinyl polymer, or the like.

The pharmaceutical composition is provided in solid, liquid or semi-solid form. A solid preparation may be prepared by blending the above components to provide a powdery composition. Alternatively, the pharmaceutical composition is provided as lyophilized preparation. The liquid preparation is provided preferably as aqueous solution, aqueous suspension, oil suspension or microcapsule composition. A semi-solid composition is provided preferably as hydrous or oily gel or ointment. About 0.001 to 60 w/v %, preferably about 0.05 to 25 w/v % of the active agent is provided in the composition.

A solid composition may be prepared by mixing an excipient with a solution of the active agent comprised in the composition of the invention, gradually adding a small quantity of water, and kneading the mixture. After drying, preferably in vacuo, the mixture is pulverized. A liquid composition may be prepared by dissolving, suspending or emulsifying the active compound in water, a buffer solution or the like. An oil suspension may be prepared by suspending or emulsifying the active compound in an oleaginous base, such as sesame oil, olive oil, corn oil, soybean oil, cottonseed oil, peanut oil, lanolin, petroleum jelly, paraffin, Isopar, silicone oil, fatty acids of 6 to 30 carbon atoms or the corresponding glycerol or alcohol esters. Buffers include Sorensen buffer [Ergeb Physiol, (1912) 12:393], Clark-Lubs buffer [J Bact (1917) 2(1):109 and 191]. MacIIvaine buffer [J Biol Chem (1921) 49:183], Michaelis buffer (Die Wasserstoffinonenkonzentration, p. 186, 1914), and Kolthoff buffer [Biochem Z, (1926) 179:410].

A composition may be prepared as a hydrous gel, e.g. for transnasal administration. A hydrous gel base is dissolved or dispersed in aqueous solution containing a buffer, and the said active agent, and the solution warmed or cooled to give a stable gel.

Preferably, the composition of the invention is administered through intravenous, intramuscular or subcutaneous administration. Oral administration is expected to be less effective, particularly where the active compound is a peptide, because the peptide may be digested before being taken up. Of course, this consideration may apply less to an active peptide invention which is modified as described above, e.g., by being cyclic peptide, by containing non-naturally occurring amino acids, such as D-amino acids, or other modification which enhance the resistance of the peptide to biodegradation. Decomposition in the digestive tract may be lessened by use of certain compositions, for instance, by confining the active compounds comprised in the compositions of the invention in microcapsules such as liposomes. The pharmaceutical composition of the invention may also be administered to other mucous membranes. The pharmaceutical composition is then provided in the form of a suppository, nasal spray or sublingual tablet. The dosage of the peptide of the invention may depend upon the condition to be treated, the patient's age, body weight, and the route of administration, and will be determined by the attending physician. Doses of active agent ranging from 0.1 µg/kg to 100 mg/kg or higher, preferably from 0.5 µg/kg to 5 mg/kg, more preferably 0.1 µg/kg to 1 mg/kg, most preferably about 100 µg/kg.

The uptake of an active agent comprised in the composition of the invention, e.g. an active peptide, may be facilitated by a number of methods. For instance, a non-toxic derivative of the cholera toxin B subunit, or of the structurally related subunit B of the heal-labile enterotoxin of enterotoxic E. coli may be added to the composition, see U.S. Pat. No. 5,554,378.

Alternatively, the pharmaceutical composition of the invention may comprise a biodegradable polymer selected from poly-1,4-butylene succinate, poly-2,3-butylene succinate, poly-1,4-butylene fumarate and poly-2,3-butylene succinate, incorporating the active compound, as the pamoate, tannate, stearate or palmitate thereof. Such compositions are described e.g., in U.S. Pat. No. 5,439,688.

Additionally, a composition of the invention may be a fat emulsion. The fat emulsion may be prepared by adding to a fat or oil about 0.1–2.4 w/w of emulsifier such as a phospholipid, an emulsifying aid, a stabilizer, mixing mechanically, aided by heating and/or removing solvents, adding water and isotonic agent, and optionally, adjusting adding the pH agent, isotonic agent. The mixture is then homogenized. Preferably, such fat emulsions contain an electric charge adjusting agent, such as acidic phospholipids, fatty acids, bilic acids, and salts therof. Acidic phospholipids include phosphatidylserine, phosphatidylglycerol, phosphatidylinositol, and phosphatidic acid. Bilic acids include deoxycholic acid, and taurocholic acid. The preparation of such pharmaceutical compositions is described in U.S. Pat. No. 5,733,877.

The invention will now be described in more detail on hand of the following Examples, which are illustrative only and do not in any sense limit the scope of invention, which is defined by the appended claims.

EXAMPLES

Materials and Methods
Bacterial Cultures and Growth Analysis

Bacteria were obtained from clinical isolates cultured as part of the routine work up for H. pylori detection. No bacteria were specifically obtained for the study. Growth curve analysis was performed using five different isolates. Endoscopic diagnosis included both peptic pathologies and normal appearing mucosa. Following endoscopy, biopsies were kept in balanced salt solution for no more than one hour. Subsequently, biopsy specimens were minced and plated on chocolate or Colombia agar plats. To generate microaerophilic conditions, bacteria were grown in sealed jars, using anaerobic gas generating kits (Oxoid, BR-38) at 37° C. Bacteria were re-plated under similar conditions every 2–4 days. For experimentation, bacteria were transferred to brain-heart infusion or Brucella broth liquid media (Gibco), supplemented with 10% calf serum (Biological Industries, Beit Haemek, Israel). Each sample was inoculated with 0.02 OD 600 corresponding to $1.6 \times 10^3$ CFU/100 µL. Gastrin or control peptides were added at different concentrations as indicated.

H. pylori growth necessitates microaerophilic conditions. Repeated sampling from the same tube would result in disruption of such conditions. To overcome this problem, in each experiment, multiple samples in the number of time points assessed were used. Each sample contained identical bacterial numbers and gastrin concentrations. A different sample was assessed at each time point. Growth was assessed by OD readings.

All bacteria were obtained from clinical isolates. Growth kinetic experiments with C. jejuni were done in similar conditions as described above for H. pylori. Growth kinetic experiments with E. coli, were performed under conditions similar to the above, in an aerobic ambient.

Gastrin and Control Peptides

Gastrin 17, cholecystokinin (CCK)-8 (fragment 26–33), pentagastrin, somatostatin 14 and epidermal growth factor (EGF) were obtained from Sigma (St. Louis, Mo.). Lyophilized peptides were dissolved in a stock solution containing acetic acid and water in a ratio of 1:1 to a concentration of 1 mg/ml, as suggested by the manufacturer and diluted with sterile deionized water to the indicated concentrations.

Radioactive Gastrin Uptake

To assess labeled gastrin uptake, bacterial pellets were resuspended in 200 µl Brucella broth containing 500 nmol/l $^{125}$I-labeled gastrin (IncStar Pharmatrade). Incubation was at either 4° C. or 37° C. for 45 minutes. Bacteria were washed three times in PBS, resuspended and incubated for 30 minutes in Brucella broth containing proteinase K (Promega) at a concentration of 25 ng/ml. Subsequently, bacteria were washed, resuspended in 100 µl PBS, out of which 10 µl were blotted on nitrocellulose filters and autoradiography performed for 7 days. Incorporated $^{125}$I was quantitated using a gamma counter.

Cold Inhibition Assay

For the cold inhibition assay, bacterial pellets were resuspended in 200 µl Brucella broth containing 500 nmol/l $^{125}$I-labeled gastrin. Unlabeled gastrin in increasing concentrations (1250–5000 nmol/l) was added concurrently. Bacteria were incubated for 45 minutes at 37° C., after which they were extensively washed with PBS. Incorporation of $^{125}$I-labeled gastrin was determined using a gamma counter. As controls, bacteria were incubated with $^{125}$I-labeled gastrin (500 nmol/l) in the presence of CCK-8, pentagastrin, somatostatin or EGF at the indicated concentrations.

Results

Figure 1A:
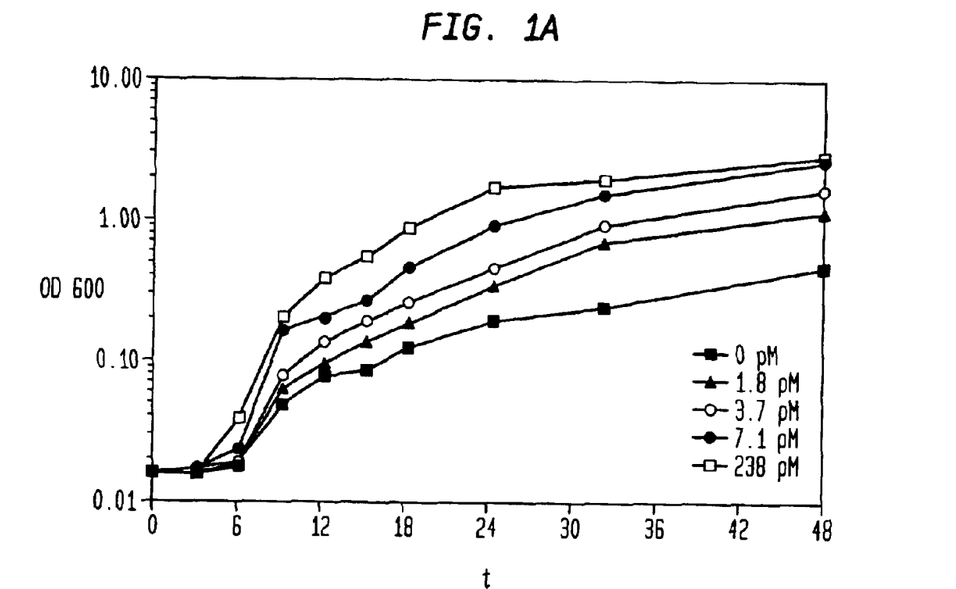
FIG. 1(A) shows a representative growth curve of one isolate over 48 hours.
Figure 1B:
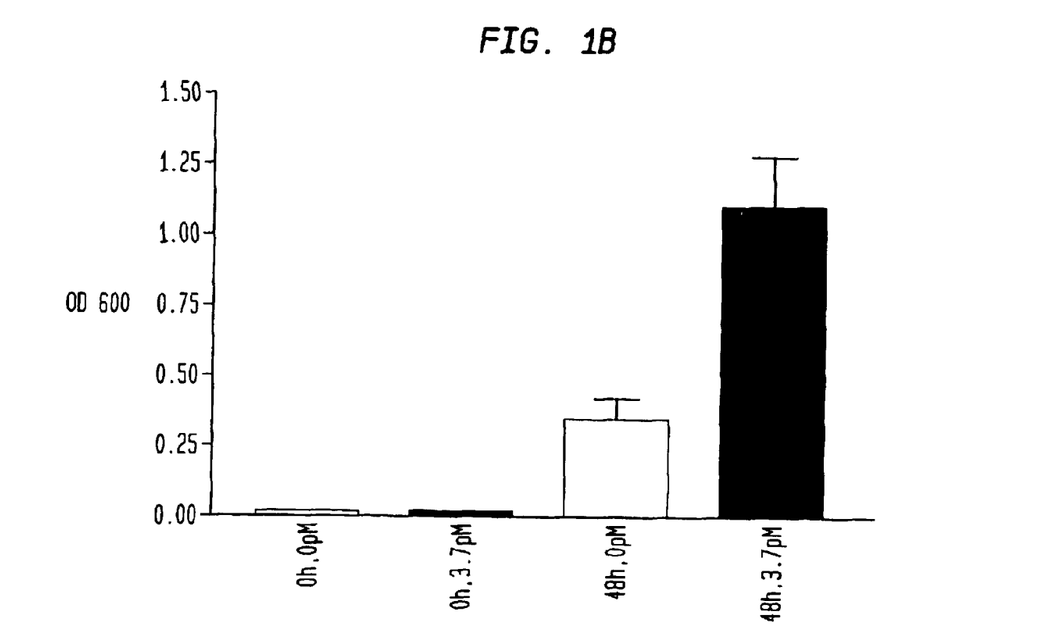
FIG. 1(B) shows cumulated growth data of 5 different clinical isolates with (3.7 pM) or without gastrin. Growth is compared at 0 h and 48 h (Shown as a mean with SEM).

To assess the effect of G17 on *H. pylori* growth, bacteria were grown with increasing gastrin concentrations. Addition of gastrin to the growth media had a dose-dependent effect on the growth curve. Gastrin shortened the lag time, increased the growth rate at the logarithmic phase and increased the final cell density at the stationary phase (FIG. 1A). FIG. 1B shows the growth of 5 different clinical isolates in the presence of gastrin at the 0 and 48h time points. As shown, a similar effect of gastrin was noted for all five isolates.

Figure 2A:
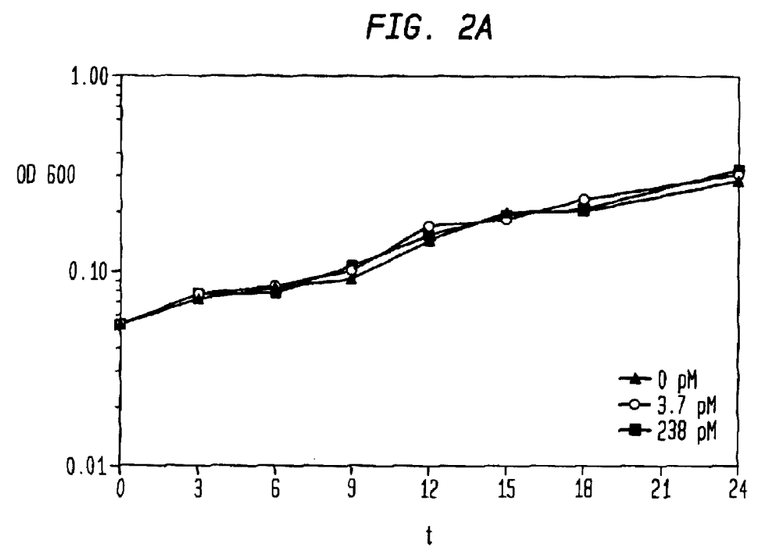
FIG. 2A: Growth kinetics analysis of C. jejuni with gastrin.
Figure 2B:
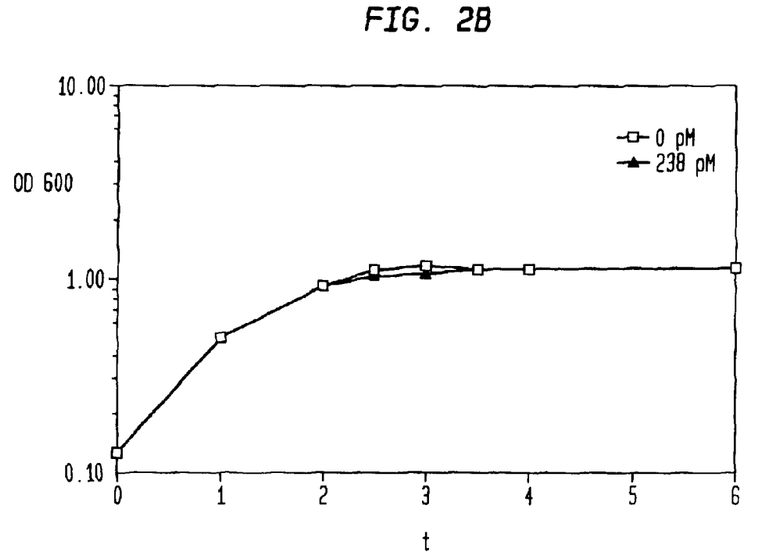
FIG. 2B:: Growth kinetics analysis of E. coli with gastrin.
Figure 2C:
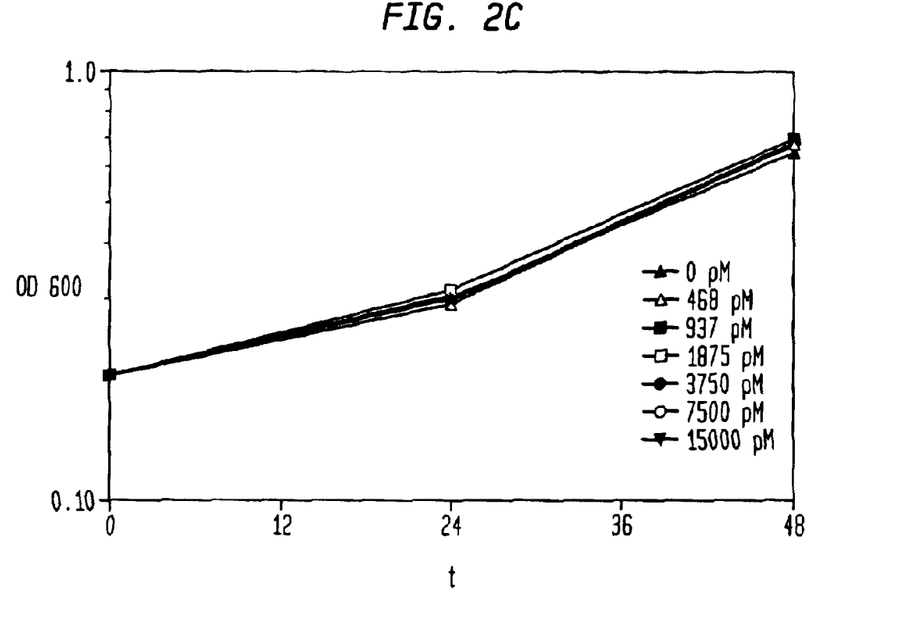
FIG. 2C: Growth kinetics analysis of H pylori with the gastric peptide somatostatm.
Figure 2D:
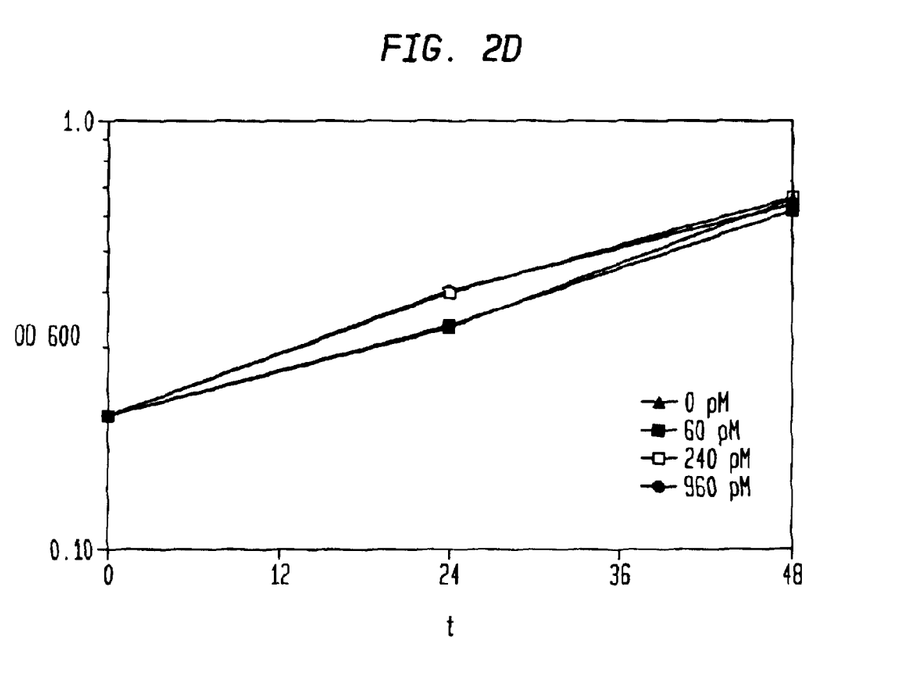
FIG. 2D: Growth kinetics analysis of H pylori with EGF.
Figure 2E:
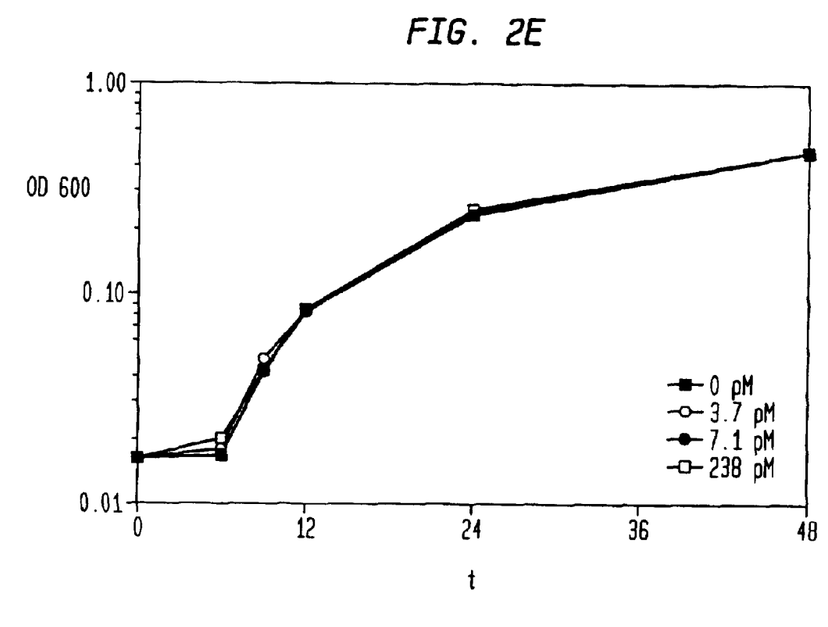
FIG. 2E: Growth kinetics analysis of H. pylori with human gastrin receptor agonist pentagastrin.
Figure 2F:
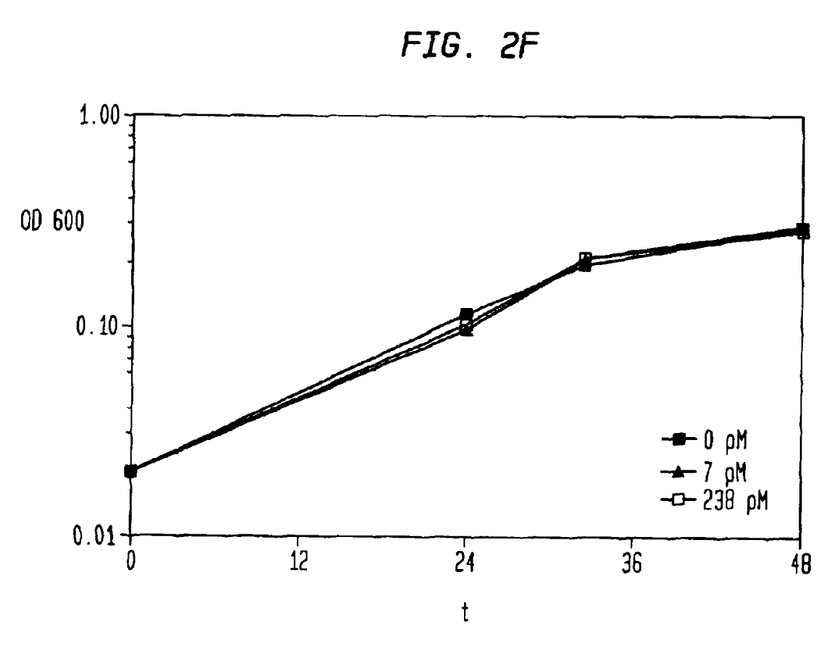
FIG. 2F: Growth kinetics analysis of H. pylori with human gastrin receptor agonist CCK-8.

To test the specificity of the gastrin effect, growth kinetic studies were done using a slow growing intestinal microaerophihic bacterium and a Gram-negative aerobic intestinal bacterium. As shown in FIGS. 2A–B, gastrin had no effect on the growth of *Campylobacter jejuni*, or *Escherichia coli*. To test whether other peptides might also have a positive growth effect similar to gastrin on *H. pylori*, *H. pylori* was grown in the presence of somatostatin, that is produced in the gastric antrum, and EGF, a growth factor peptide found within the gastric lumen. In addition, since in humans the gastrin and CCKB receptors are homologous, the gastrin/CCKB receptor agonists CCK-8 and pentagastrin, which have structural homology to gastrin, were tested for their effect on *H. pylori* growth. As shown in FIGS. 2C–F, none of the peptides had an effect on the growth of *H. pylori*, indicating that the positive growth effect of gastrin was specific.

Figure 3:
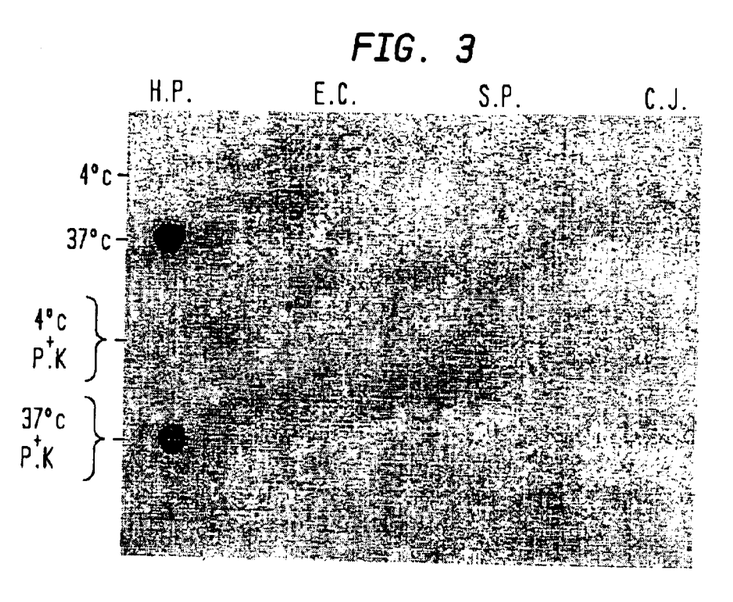
FIG. 3 Gastrin uptake assay.

To learn whether the uptake of gastrin to *H. pylori* was specific and whether gastrin was internalized by *H. pylori* or bound to the outer surface, *H. pylori* and control bacteria were incubated with $^{125}$I-labeled gastrin, at 4° C., or 37° C. Following this initial incubation, bacteria were co-incubated with proteinase K, to digest surface proteins. Labeled gastrin incorporation was assessed by autoradiography and CPM determination. As shown in FIG. 3, the uptake of gastrin by the bacteria was specific for *H. pylori*, since no labeling was noted with control bacteria. Further, only *H. pylori* incubated at 37° C. incorporated the $^{125}$I-labeled gastrin. Such temperature-dependence suggests that an energy-dependent mechanism is responsible for the uptake of gastrin. Moreover, no reduction in radioactive counts was noted following co-incubation with proteinase K (before proteinase K incubation—311 CPM, following incubation with proteinase K—385 CPM), suggesting that the gastrin entered the bacteria and thus, was protected from proteinase K digestion.

Figure 4:
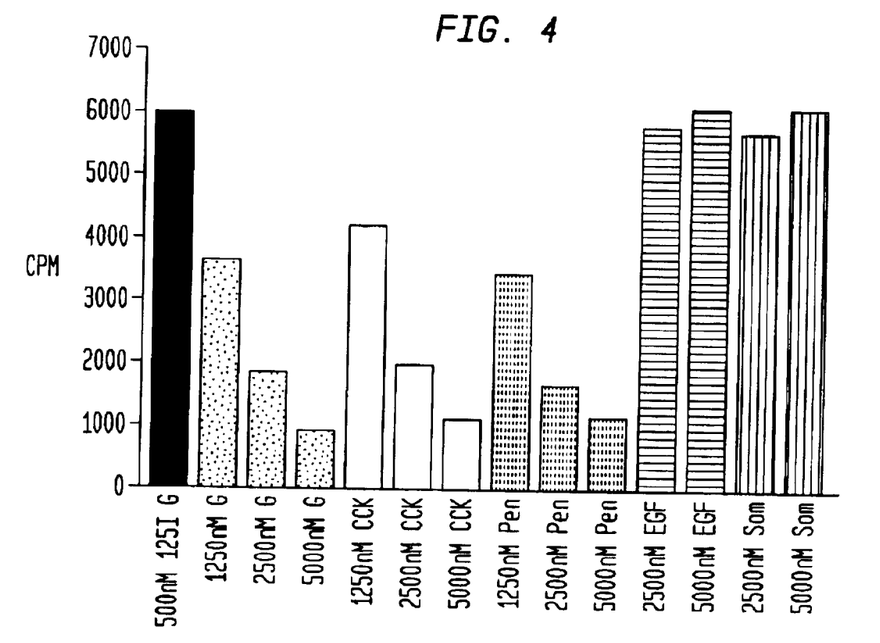
FIG. 4 Competition by diferent peptides on $^{125}$I-labeled gastrin uptake by H. pylori.

To test whether gastrin entered the bacteria by a nonspecific mechanism or, by interaction with a specific binding site, uptake of labeled gastrin was competed, using unlabeled gastrin and control peptides. As shown in FIG. 4, the uptake of labeled gastrin by *H. pylori* could be inhibited with an excess of unlabeled gastrin. Similar to unlabeled gastrin, co-incubation of bacteria in the presence of CCK-8 and pentagastrin inhibited labeled gastrin uptake in a dose-dependent manner. In contrast, no inhibition of gastrin uptake was shown by EGF or somatostatin.

The cold-ligand competition and inhibition of gastrin uptake by peptides known to activate shared receptors in humans, the temperature profile of gastrin binding and the protection against proteinase K digestion, all suggest the internal localization of a putative receptor or channel with specific structural restriction.

What is claimed is:

1. A method of treating or ameliorating an *Helicobacter pylori*-associated disease in a patient in need of such, comprising administering to said patient an amount of a peptide comprising SEQ ID NO:1 effective to inhibit the growth of *Helicobacter pylori*, thereby treating or ameliorating the *Helicobacter pylori*-associated disease by inhibiting the growth of *Helicobacter pylori*, wherein the *Helicobacter pylori*-associated disease is a *Helicobacter pylori*-associated gastrointestinal disease.

2. The method of claim 1, wherein said peptide is a fragment of gastrin or a synthetic analog of gastrin.

3. The method of claim 2, wherein said peptide is pentagastrin, an active fragment thereof, or a synthetic analog of pentagastrin.

4. The method of claim 1, wherein said peptide is cholecystokinin (CCK)-8, an active fragment thereof, or a synthetic analog of CCK-8.

5. The method of claim 1, wherein said peptide is an inhibitor of gastrin uptake by *Helicobacter pylori*.

6. The method of claim 5, wherein said inhibitor is a competitive gastrin uptake inhibitor.

7. The method of claim 1, wherein said gastrointestinal disease is selected from the group consisting of gastric peptic ulcer, duodenal peptic ulcer, gastritis, duodenitis, non-ulcer dyspepsia and gastric carcinoma.

8. A method of inhibiting the growth-enhancing effect of gastrin on *Helicobacter pylori* comprising contacting said *Helicobacter pylori* with an effective amount of a peptide comprising SEQ ID NO:1, wherein the peptide inhibits the growth-enhancing effect of gastrin on *Helicobacter pylori* thereby inhibiting the growth-enhancing effect of gastrin on *Helicobacter pylori*.

9. The method of claim 8, wherein said peptide is a fragment of gastrin or a synthetic analog of gastrin.

10. The method of claim 9, wherein said peptide is pentagastrin, an active fragment thereof, or a synthetic analog of pentagastrin.

11. The method of claim 8, wherein said peptide is cholecystokimin (CCK)-8, an active fragment thereof, or a synthetic analog of CCK-8.

12. The method of claim 8, wherein said peptide is a competitive inhibitor of gastrin uptake by *Helicobacter pylori*.

13. The method of claim 8, wherein said peptide is administered in a dose of 0.5 µg to 5 mg per kg of body weight.

14. The method of claim 8, wherein said peptide is administered in a dose of 0.1 µg to 1 mg per kg of body weight.

15. The method of claim 1, wherein said peptide is administered in a dose of 0.5 µg to 5 mg per kg of body weight.

16. The method of claim 1, wherein said peptide is administered in a dose of 0.1 µg to 1 mg per kg of body weight.

* * * * *

UNITED STATES PATENT AND TRADEMARK OFFICE
CERTIFICATE OF CORRECTION

PATENT NO. : 6,815,414 B2
DATED : November 9, 2004
INVENTOR(S) : Chowers et al.

It is certified that error appears in the above-identified patent and that said Letters Patent is hereby corrected as shown below:

Title page,
Item [65], Prior Publication Data, delete "US 2003/0069188 A1 Apr. 10, 2003" and insert -- US 2001/0020005 A1 Sep. 6, 2001 --.
Item [56], References Cited, OTHER PUBLICATIONS,
"Konturek, J.W. et al." reference, after "restores the inhibitory effect of", delete "choloecystokinin" and insert -- cholecystokinin --.

Column 12,
Line 2, delete "cholecystokimin" and insert -- cholecystokinin --.

Signed and Sealed this

First Day of February, 2005

JON W. DUDAS
*Director of the United States Patent and Trademark Office*